(12) United States Patent
Muller et al.

(10) Patent No.: US 7,872,098 B1
(45) Date of Patent: Jan. 18, 2011

(54) PHOSPHORYLATED DERIVATIVES OF A U1-70K PEPTIDE AND THEIR USE IN THE TREATMENT OF AUTOIMMUNE PATHOLOGIES

(75) Inventors: Sylviane Muller, Strasbourg (FR); Fanny Sylvie Michele Monneaux, La Wantzenau (FR); Jean-Paul Briand, Strasbourg (FR); Gilles Guichard, Wolfisheim (FR); Jean-Gerard Guillet, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 1807 days.

(21) Appl. No.: 10/489,967

(22) PCT Filed: Sep. 18, 2002

(86) PCT No.: PCT/FR02/03186

§ 371 (c)(1),
(2), (4) Date: Aug. 17, 2004

(87) PCT Pub. No.: WO03/025014

PCT Pub. Date: Mar. 27, 2003

(30) Foreign Application Priority Data

Sep. 18, 2001 (FR) .................................. 01 12041

(51) Int. Cl.
  *A61K 38/04* (2006.01)

(52) U.S. Cl. ..................................................... 530/326
(58) Field of Classification Search ....................... None
  See application file for complete search history.

(56) References Cited

FOREIGN PATENT DOCUMENTS

WO   WO 03/020747 A1 * 3/2003

OTHER PUBLICATIONS

Monneaux, F., et al. J. Immunol. 2001;175:5839-5847.*
Brahms Hero et al: "The C-terminal RG dipeptide repeats of the spliceosomal Sm proteins D1 and D3 contain symmetrical dimethylarginines, which form a major B-ell epitope for anti-Sm Autoantibodies." Journal of Biological Chemistry, vol. 275, No. 22, Jun. 2, 2000, pp. 17122-17129, XP002202537.
Monneaux Fanny et al: "B and T cell immune response to small nuclear ribonucleoprotein particles in lupus mice: Autoreactive CD4+ T cells recognize a T cell epitope located within the RNP80 motif of the 70K protein." European Journal of Immunology, vol. 30, No. 8, Aug. 2000, pp. 2191-2200, XP002202538.
Monneaux F et al: "Key sequences involved in the spreading of the systemic autoimmune response to spliceosomal proteins." Scandinavian Journal of Immunology, vol. 54, No. 1-2, Jul. 2001, pp. 45-54, XP002202539.

* cited by examiner

*Primary Examiner*—G. R Ewoldt
(74) *Attorney, Agent, or Firm*—Young & Thompson

(57) ABSTRACT

Derivatives of the peptide corresponding to the sequence RIHMVYSKRSGKPRGYAFIEY (SEQ ID NO: 1), pharmaceutical compositions, and methods of use thereof are provided.

5 Claims, 19 Drawing Sheets

| HLA-DR molecules | % of binding | | |
|---|---|---|---|
| | 131-151 | P140 | Indicator peptide |
| HLA-DR1 | 76.9 ± 4.1 | 63.8 ± 2.4 | 0 |
| HLA-DR4 | 72.8 ± 7.4 | 70.2 ± 1.9 | 0 |
| HLA-DR11 | 58.3 ± 17.7 | 46.4 ± 0.7 | 7.1 ± 1.0 |

Figure 19

SEQUENCE LISTING

```
<160> NUMBER OF SEQ ID NOS: 1

<210> SEQ ID NO 1
<211> LENGTH: 21
<212> TYPE: PRT
<213> ORGANISM: Homo sapiens

<400> SEQUENCE: 1

Arg Ile His Met Val Tyr Ser Lys Arg Ser Gly Lys Pro Arg Gly Tyr
1               5                   10                  15

Ala Phe Ile Glu Tyr
            20
```

PHOSPHORYLATED DERIVATIVES OF A U1-70K PEPTIDE AND THEIR USE IN THE TREATMENT OF AUTOIMMUNE PATHOLOGIES

A subject of the present invention is novel peptides transformed so as to comprise post-translational-type modifications, such as phosphorylation or acetylation of one or more amino acids. The invention also relates to processes for obtaining them, and their uses in pharmaceutical compositions within the framework of the treatment of autoimmune pathologies.

Several studies have shown the benefits of using synthetic peptides for the prevention in murine models of the development of autoimmune pathologies such as lupus. These studies have been carried out with peptides derived either from histone sequences, or from anti-DNA antibodies. The administration by intravenous route of these peptides has allowed a reduction in the production of anti-DNA antibodies typical of lupus and a prolongation of the survival of the treated mice. No study has been carried out based on protein sequences of the spliceosome, another lupus autoantigen.

The few studies carried out to date having shown an improvement of the pathology of lupus in autoimmune mice have used peptides not containing post-translational modifications (Eilat et al., 2000; Jouanne et al., 1999; Kaliyaperumal et al., 1999; Marino et al, 2000).

The post-translational modifications seem to play an important role in the emergence of the autoimmune response (Utz and Anderson, 1998). In order to establish effective intervention strategies, the identification of the targets which are really responsible for the rupture of the self-tolerance and then recognized by the autoreactive cells is a major benefit.

The identification of the sequences of the 70K protein recognized by the autoreactive T-cells began in 1998. The inventors firstly synthesized 20 overlapping peptides covering the sequence of the 70K protein and studied recognition of these peptides by the antibodies of MRL/lpr lupic mice and by the autoreactive CD4+ T cells of these mice. Among these 20 peptides, they identified the peptide corresponding to the sequence 131-151 (RIHMVYSKRSGKPRGYAFIEY) of the 70K protein recognized very early by the antibodies of these mice (Monneaux et al, 2000). This peptide is capable of stimulating in vitro the proliferation and the secretion of IL-2 by the CD4+ T cells purified from the ganglia.

Figure 1:
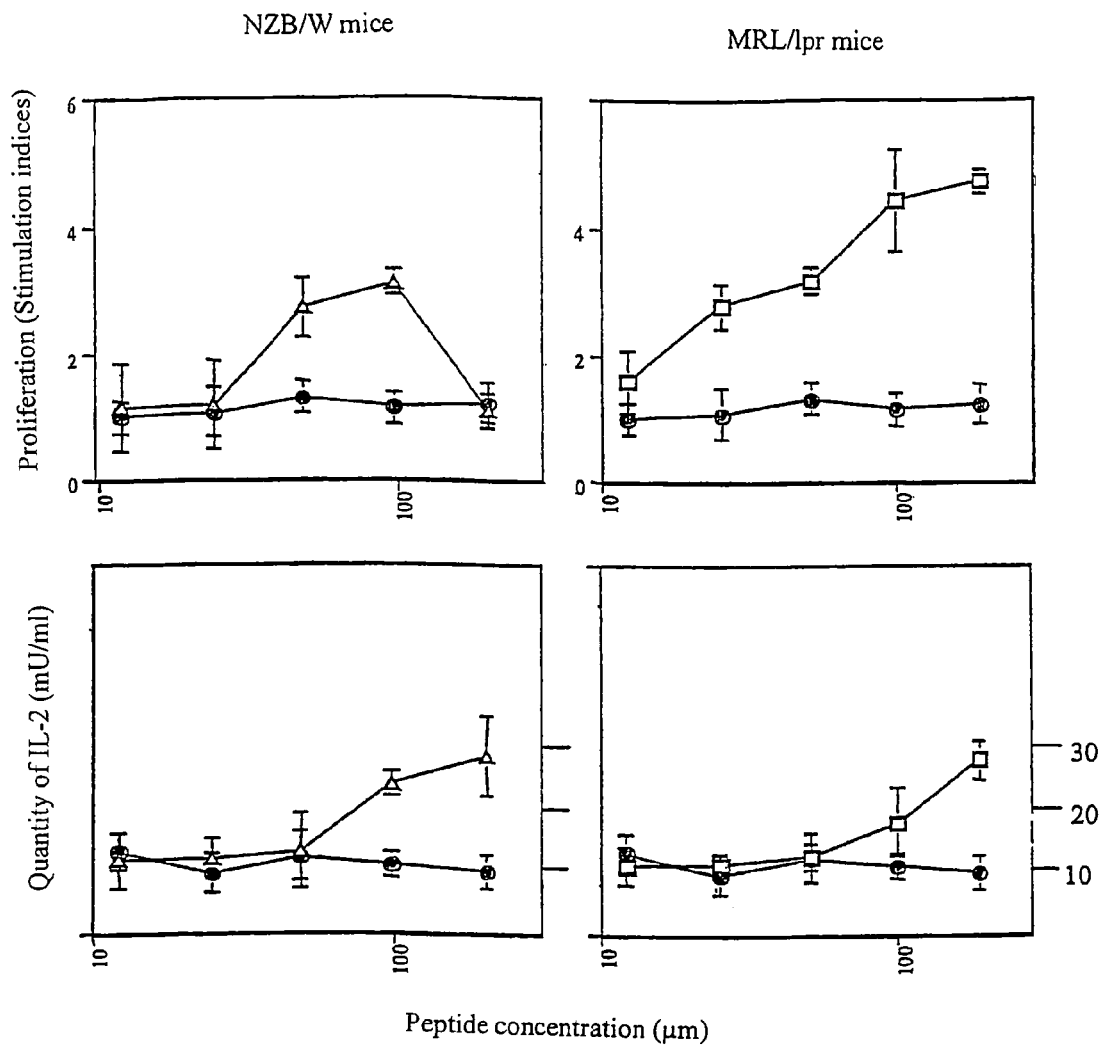
Figure 2:
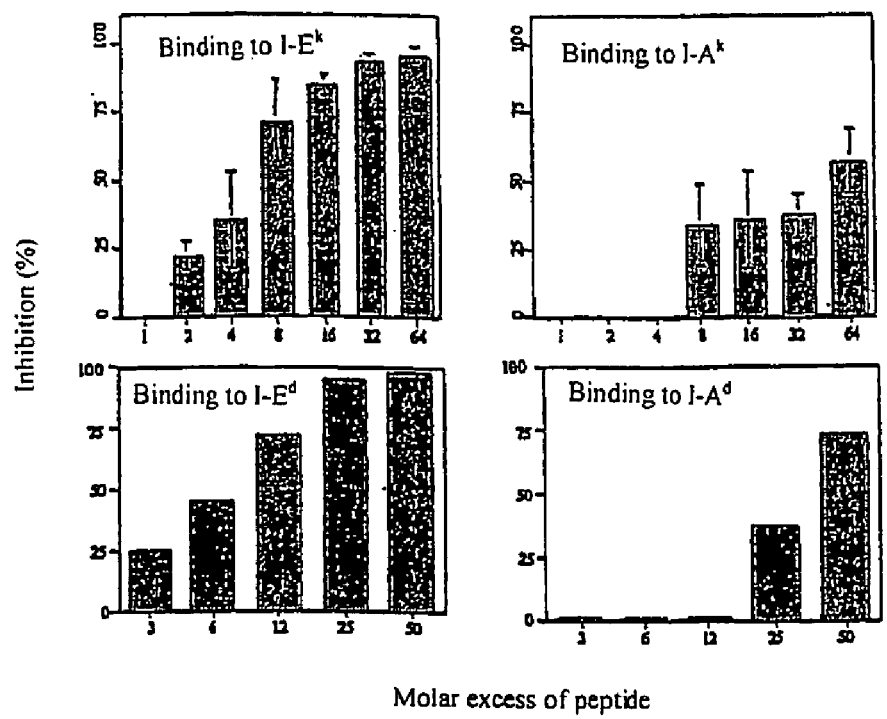

Subsequently, the inventors showed that this sequence also represented a major epitope of the 70K protein in another model of lupic mice, the NZB/W mouse (FIG. 1). The 131-151 peptide is moreover capable of binding to various major histocompatibility complex class II molecules (both murine, and human; FIG. 2). This universal character constitutes an advantage for the use of this sequence in the development of therapeutic strategies within the framework of human systemic lupus erythematosus.

The inventors then wished to determine the exact nature of the sequence of the 70K protein capable of activating the autoreactive T cells. The inventors synthesized several peptides corresponding to the phosphorylated and acetylated forms on the serine and lysine residues of the 131-151 peptide, and studied the ability of these peptides to be recognized by the T lymphocytes and the antibodies of lupic mice.

The present invention derives from the demonstration by the inventors that these phosphorylated and acetylated peptides are recognized to the same extent or even to a greater extent than the non-phosphorylated and non-acetylated parent peptide by the CD4+ T cells and the antibodies of lupic mice, and that the administration of these phosphorylated and acetylated peptides reduces the production of large amounts of antibodies directed against the DNA, delays the appearance of glomerulonephritis and prolongs the survival of the animals, while the parent peptide does not on the other hand induce any statistically significant effect.

An aim of the present invention is to provide novel peptides which can be used for the preparation of medicaments within the framework of the treatment of autoimmune diseases, and more particularly of lupus, which have the advantage of being clearly more effective than the peptides used to date, and not having major side effects such as those encountered with the current treatment techniques, to the extent that the modified peptides of the invention are specific to the deleterious cells and only target these cells, unlike the immunosuppressives, cytokines, or other molecules currently used which act on the immune system in a global fashion.

A subject of the invention is the use of peptides comprising epitopes of self-proteins of mammals recognized by antibodies produced by the immune system of mammals suffering from autoimmune pathologies, and, if appropriate, by the auxiliary T cells of said mammals, said epitopes being such that at least one of their amino acids comprises a post-translational modification, for the preparation of a medicament intended for the prevention or the treatment of said autoimmune pathologies.

By post-translational modification, is meant in the preceding and in the following, any type of modification of the amino acids of a given protein capable of being produced in vivo in the cells of the organism, such as the phosphorylation or acetylation processes or other processes.

A subject of the invention is more particularly the above-mentioned use of peptides as defined above, comprising epitopes in which at least one of their amino acids is modified in such a manner that it is in a phosphorylated, or acetylated form.

The invention more particularly relates to the above-mentioned use of peptides comprising epitopes originating from proteins of human or animal origin defined above, said proteins being chosen from the nucleoproteins, the proteins of the nucleosome, spliceosome, Ro ribonucleoproteic particle, or ribosome for example.

The invention also relates to the use of peptides as defined above, for the preparation of a medicament intended for the prevention or treatment:
- of autoimmune pathologies of the family of connective tissue diseases (non-organ-specific systemic diseases), such as systemic lupus erythematosus (SLE), rheumatoid arthritis, mixed connective tissue disease, Sjögren's syndrome, or chronic juvenile arthritis,
- or of organ-specific autoimmune pathologies, such as multiple sclerosis, insulin-dependent diabetes, Crohn's disease, or bullous diseases.

A subject of the invention is more particularly the use of peptides as defined above, for the preparation of a medicament intended for the prevention or the treatment of SLE.

Therefore, the invention relates more particularly to the above-mentioned use of peptides comprising epitopes originating from the human or murine U1-70K protein of the spliceosome (described in particular in Klein Gurnewiek et al, 1997).

A subject of the invention is still more particularly the above-mentioned use of peptides comprising the sequence delimited by the 131 and 151 amino acids of the human or murine U1-70K protein, and corresponding to the following sequence SEQ ID NO: 1:

RIHMVYSKRSGKPRGYAFIEY in which at least one of the amino acids comprises a post-translational-type modification, in particular in which at least one of the amino acids is phosphorylated, or acetylated.

The invention relates more particularly to the above-mentioned use of peptides comprising the sequence SEQ ID NO: 1 in which at least one of the serine residues in position 7 or 10 is phosphorylated, and/or at least one of the lysine residues in position 8 or 12 is acetylated.

A subject of the invention is more particularly the above-mentioned use of peptides comprising the sequence SEQ ID NO: 1 in which:
  the serine in position 7 is phosphorylated,
  and/or the serine in position 10 is phosphorylated,
  and/or the lysine in position 8 is acetylated,
  and/or the lysine in position 12 is acetylated.

The invention relates still more particularly to the above-mentioned use of peptides chosen from the following:
  the sequence SEQ ID NO: 1 in which the serine in position 7 is phosphorylated,
  the sequence SEQ ID NO: 1 in which the serine in position 7 as well as the serine in position 10 are phosphorylated,
  the sequence SEQ ID NO: 1 in which the serine in position 7 is phosphorylated, and the lysine in position 8 is acetylated,
  the sequence SEQ ID NO: 1 in which the serine in position 7 is phosphorylated, and the lysine in position 12 is acetylated,
  the sequence SEQ ID NO: 1 in which the serine in position 7 is phosphorylated, and the lysine in position 8 as well as the lysine in position 12 are acetylated,
  the sequence SEQ ID NO: 1 in which the serine in position 7 as well as the serine in position 10 are phosphorylated, and the lysine in position 8 is acetylated,
  the sequence SEQ ID NO: 1 in which the serine in position 7 and the serine in position 10 are phosphorylated, and the lysine in position 12 is acetylated,
  the sequence SEQ ID NO: 1 in which the serine in position 7 as well as the serine in position 10 are phosphorylated, and the lysine in position 8 as well as the lysine in position 12 are acetylated,
  the sequence SEQ ID NO: 1 in which the serine in position 10 is phosphorylated,
  the sequence SEQ ID NO: 1 in which the serine in position 10 is phosphorylated, and the lysine in position 8 is acetylated,
  the sequence SEQ ID NO: 1 in which the serine in position 10 is phosphorylated, and the lysine in position 12 is acetylated,
  the sequence SEQ ID NO: 1 in which the serine in position 10 is phosphorylated, and the lysine in position 8 as well as the lysine in position 12 are acetylated,
  the sequence SEQ ID NO: 1 in which the lysine in position 8 is acetylated,
  the sequence SEQ ID NO: 1 in which the lysine in position 12 is acetylated,
  the sequence SEQ ID NO: 1 in which the lysine in position 8 and the lysine in position 12 are acetylated.

A subject of the invention is still more particularly the above-mentioned use of peptides chosen from the following:
  the sequence SEQ ID NO: 1 in which the serine in position 7 is phosphorylated,
  the sequence SEQ ID NO: 1 in which the serine in position 10 is phosphorylated,
  the sequence SEQ ID NO: 1 in which the lysine in position 8 is acetylated,
  the sequence SEQ ID NO: 1 in which the lysine in position 12 is acetylated,
  the sequence SEQ ID NO: 1 in which the lysine in position 8 and the lysine in position 12 are acetylated.

A subject of the invention is also any pharmaceutical composition characterized in that it comprises at least one peptide chosen from those defined above, in combination with a pharmaceutically acceptable vehicle.

A subject of the invention is more particularly any pharmaceutical composition as defined above, characterized in that it comprises at least one peptide chosen from those comprising the sequence SEQ ID NO: 1 in which at least one of the amino acids comprises a post-translational-type modification, in particular by phosphorylation, or acetylation.

The invention relates more particularly to any pharmaceutical composition as defined above, characterized in that it comprises at least one peptide chosen from those comprising the sequence SEQ ID NO: 1 in which at least one of the serine residues in position 7 or 10 is phosphorylated, and/or at least one of the lysine residues in position 8 or 12 is acetylated.

A subject of the invention is more particularly any pharmaceutical composition as defined above, characterized in that it comprises at least one peptide chosen from those comprising the sequence SEQ ID NO: 1 in which:
  the serine in position 7 is phosphorylated,
  and/or the serine in position 10 is phosphorylated,
  and/or the lysine in position 8 is acetylated,
  and/or the lysine in position 12 is acetylated.

The invention relates still more particularly to any pharmaceutical composition as defined above, characterized in that it comprises at least one peptide chosen from the following:
  the sequence SEQ ID NO: 1 in which the serine in position 7 is phosphorylated,
  the sequence SEQ ID NO: 1 in which the serine in position 7 as well as the serine in position 10 are phosphorylated,
  the sequence SEQ ID NO: 1 in which the serine in position 7 is phosphorylated, and the lysine in position 8 is acetylated,
  the sequence SEQ ID NO: 1 in which the serine in position 7 is phosphorylated, and the lysine in position 12 is acetylated,
  the sequence SEQ ID NO: 1 in which the serine in position 7 is phosphorylated, and the lysine in position 8 as well as the lysine in position 12 are acetylated,
  the sequence SEQ ID NO: 1 in which the serine in position 7 as well as the serine in position 10 are phosphorylated, and the lysine in position 8 is acetylated,
  the sequence SEQ ID NO: 1 in which the serine in position 7 as well as the serine in position 10 are phosphorylated, and the lysine in position 12 is acetylated, the sequence SEQ ID NO: 1 in which the serine in position 7 as well as the serine in position 10 are phosphorylated, and the lysine in position 8 as well as the lysine in position 12 are acetylated, the sequence SEQ ID NO: 1 in which the serine in position 10 is phosphorylated, the sequence SEQ ID NO: 1 in which the serine in position 10 is phosphorylated, and the lysine in position 8 is acetylated, the sequence SEQ ID NO: 1 in which the serine in position 10 is phosphorylated, and the lysine in position 12 is acetylated, the sequence SEQ ID NO: 1 in which the serine in position 10 is phosphorylated, and the lysine in position 8 as well as the lysine in position 12 are acetylated, the sequence SEQ ID NO: 1 in which the lysine in position 8 is acetylated, the sequence SEQ ID NO: 1 in which the lysine in position 12 is acetylated, the sequence SEQ ID NO: 1 in which the lysine in position 8 and the lysine in position 12 are acetylated.

A subject of the invention is still more particularly any pharmaceutical composition as defined above, characterized in that it comprises at least one peptide chosen from the following:

the sequence SEQ ID NO: 1 in which the serine in position 7 is phosphorylated, the sequence SEQ ID NO: 1 in which the serine in position 10 is phosphorylated, the sequence SEQ ID NO: 1 in which the lysine in position 8 is acetylated, the sequence SEQ ID NO: 1 in which the lysine in position 12 is acetylated, the sequence SEQ ID NO: 1 in which the lysine in position 8 and the lysine in position 12 are acetylated.

Advantageously, the above-mentioned pharmaceutical compositions of the invention, are characterised in that they are presented in a form which can be administered by systemic route (namely by intravenous, intramuscular, intraperitoneal, subcutaneous route), or non-invasively (for example by intranasal, oral, or epicutaneous route).

Advantageously also, the above-mentioned pharmaceutical compositions of the invention, are characterised in that the daily doses of peptides for a human are from approximately 100 ng to approximately 5 mg.

The invention also relates to the peptides comprising the sequence delimited by the amino acids 131 and 151 of the human or murine U1-70K protein, and corresponding to the sequence SEQ ID NO: 1 as follows: RIHMVYSKRSGKPR-GYAFIEY in which at least one of the amino acids is phosphorylated, or acetylated.

A subject of the invention is more particularly the above-mentioned peptides, comprising the sequence SEQ ID NO: 1 in which at least one of the serine residues in position 7 or 10 is phosphorylated, and/or at least one of the lysine residues in position 8 or 12 is acetylated.

The invention relates more particularly to the above-mentioned peptides, comprising the sequence SEQ ID NO: 1 in which:

the serine in position 7 is phosphorylated, and/or the serine in position 10 is phosphorylated, and/or the lysine in position 8 is acetylated, and/or the lysine in position 12 is acetylated.

The invention relates still more particularly to the following peptides:

the sequence SEQ ID NO: 1 in which the serine in position 7 is phosphorylated, the sequence SEQ ID NO: 1 in which the serine in position 7 as well as the serine in position 10 are phosphorylated, the sequence SEQ ID NO: 1 in which the serine in position 7 is phosphorylated, and the lysine in position 8 is acetylated, the sequence SEQ ID NO: 1 in which the serine in position 7 is phosphorylated, and the lysine in position 12 is acetylated, the sequence SEQ ID NO: 1 in which the serine in position 7 is phosphorylated, and the lysine in position 8 as well as the lysine in position 12 are acetylated, the sequence SEQ ID NO: 1 in which the serine in position 7 as well as the serine in position 10 are phosphorylated, and the lysine in position 8 is acetylated, the sequence SEQ ID NO: 1 in which the serine in position 7 as well as the serine in position 10 are phosphorylated, and the lysine in position 12 is acetylated, the sequence SEQ ID NO: 1 in which the serine in position 7 as well as the serine in position 10 are phosphorylated, and the lysine in position 8 as well as the lysine in position 12 are acetylated, the sequence SEQ ID NO: 1 in which the serine in position 10 is phosphorylated, the sequence SEQ ID NO: 1 in which the serine in position 10 is phosphorylated, and the lysine in position 8 is acetylated, the sequence SEQ ID NO: 1 in which the serine in position 10 is phosphorylated, and the lysine in position 12 is acetylated, the sequence SEQ ID NO: 1 in which the serine in position 10 is phosphorylated, and the lysine in position 8 as well as the lysine in position 12 are acetylated, the sequence SEQ ID NO: 1 in which the lysine in position 8 is acetylated, the sequence SEQ ID NO: 1 in which the lysine in position 12 is acetylated, the sequence SEQ ID NO: 1 in which the lysine in position 8 as well as the lysine in position 12 are acetylated.

A subject of the invention is still more particularly the following peptides:

the sequence SEQ ID NO: 1 in which the serine in position 7 is phosphorylated, the sequence SEQ ID NO: 1 in which the serine in position 10 is phosphorylated, the sequence SEQ ID NO: 1 in which the lysine in position 8 is acetylated, the sequence SEQ ID NO: 1 in which the lysine in position 12 is acetylated, the sequence SEQ ID NO: 1 in which the lysine in position 8 and the lysine in position 12 are acetylated.

The invention is further illustrated using the detailed description which follows of the synthesis of the modified peptides of the invention, as well as the study of their biological properties.

I) Syntheses

The phosphorylated peptides P137 (corresponding to the sequence SEQ ID NO: 0.1 in which the serine in position 7 is phosphorylated), and P140 (corresponding to the sequence SEQ ID NO: 1 in which the serine in position 10 is phosphorylated), and the Ac138 acetylated peptides (corresponding to the sequence SEQ ID NO: 1 in which the lysine in position 8 is acetylated), Ac142 (corresponding to the sequence SEQ ID NO: 1 in which the lysine in position 12 is acetylated), and Ac138+142 (corresponding to the sequence SEQ ID NO: 1 in which the lysine in position 8 and that in position 12 are acetylated), as well as the scrambled peptide Sc: YVSRYFG-SAIRHEPKMKIYRG, and the scrambled peptide ScP corresponding to Sc in which the serine in position 8 is phosphorylated, (used as negative controls in the tests which follow) corresponding respectively to the sequence SEQ ID NO: 1 and to the P140 sequence in which the amino acids are in a different and random order, were chemically synthesized in solid phase on an automatic synthesizer using the Fmoc strategy (N-(9-fluorenyl)methoxycarbonyl). In order to introduce the phosphorylated serine residues in place of the serine residues or the acetylated lysine residues in place of the lysine residues, an Fmoc-Ser(PO(Obz)OH)-OH-type serine derivative, or an Fmoc-Lys (Ac)-type lysine derivative, were used. The coupling time is increased to 30 minutes and a second coupling is carried out systematically. After cleavage in acid medium, each peptide is precipitated by cold ether, solubilized in a solution of water and acetonitrile and finally lyophilized. The peptides are then purified by RP-HPLC, their integrity and their purity have been analyzed by analytic HPLC and by mass spectrometry (Maldi-TOF).

|  | Purity | Expected mass | Measured mass |
| --- | --- | --- | --- |
| P137 | 71.1% | 2639 | 2637.04 |
| P140 | 90.2% | 2639 | 2637.03 |
| Ac138 | 88.8% | 2600 | 2602.3 |
| Ac142 | 83.4% | 2600 | 2600.3 |
| Ac138 + 142 | 85.1% | 2643 | 2644.68 |
| Sc | 96.5% | 2558 | 2559.56 |
| ScP | 97.2% | 2637 | 2637.06 |

The HPLC profiles of the P137, P140, Ac138, Ac142, Ac138+142, Sc and ScP peptides are represented respectively in FIGS. 3, 4, 5, 6, 7, 15 and 16 (equipment used: Nucifosil column C 1B 150×4.6 mm; flow rate: 1.2 ml/mn; UV detection: 210 nm; gradient used: 5-65 over 20 minutes in water+ 0.1% TFA and acetonitrile+0.08% TFA).

The results are shown in Tables A, B, C, D, E, F and G below corresponding respectively to the HPLC profiles of the P137, P140, Ac 138, Ac 142, Ac 138+142, Sc and ScP peptides.

TABLE A

| number of peaks | retention time | peak area | area percentage |
| --- | --- | --- | --- |
| 1 | 12.16 | 164.7 | 71.1 |
| 2 | 12.39 | 60.5 | 26.1 |
| 3 | 12.63 | 6.6 | 2.3 |
| Total |  | 231.8 | 100.0 |

TABLE B

| number of peaks | retention time | peak area | area percentage |
| --- | --- | --- | --- |
| 1 | 11.93 | 8.9 | 3.1 |
| 2 | 12.13 | 254.4 | 90.2 |
| 3 | 12.45 | 11.5 | 4.1 |
| 4 | 12.72 | 7.3 | 2.6 |
| Total |  | 292.1 | 100.0 |

TABLE C

| number of peaks | retention time | peak area | area percentage |
| --- | --- | --- | --- |
| 1 | 12.67 | 171.6 | 88.8 |
| 2 | 12.83 | 21.7 | 11.2 |
| Total |  | 193.3 | 100.0 |

TABLE D

| number of peaks | retention time | peak area | area percentage |
| --- | --- | --- | --- |
| 1 | 11.39 | 1.9 | 0.8 |
| 2 | 12.75 | 203.1 | 83.4 |
| 3 | 12.92 | 34.8 | 14.2 |
| 4 | 13.22 | 3.8 | 1.6 |
| Total |  | 243.6 | 100.0 |

TABLE E

| number of peaks | retention time | peak area | area percentage |
| --- | --- | --- | --- |
| 1 | 13.03 | 213.3 | 85.1 |
| 2 | 13.22 | 15.2 | 6.1 |
| 3 | 13.37 | 22.1 | 8.8 |
| Total |  | 250.6 | 100.0 |

TABLE F

| Number of peaks | retention time | peak area | area percentage |
| --- | --- | --- | --- |
| 1 | 12.08 | 219.3 | 96.5 |
| 2 | 12.67 | 2.5 | 1.1 |
| 3 | 12.63 | 5.5 | 2.4 |
| Total |  | 227.2 | 100.0 |

TABLE G

| Number of peaks | retention time | peak area | area percentage |
| --- | --- | --- | --- |
| 1 | 12.39 | 273.4 | 97.2 |
| 2 | 12.93 | 2.4 | 0.9 |
| 3 | 13.63 | 5.4 | 1.9 |
| Total |  | 281.2 | 100.0 |

The mass spectra of the P137, P140, Ac 138, Ac 142, Ac 138+142, Sc and ScP peptides are represented respectively on FIGS. 8, 9, 10, 11, 12, 17 and 18.

II) Biological Properties

The 70K protein being strongly phosphorylated in vivo (Woppmann et al., 1993), and although the number of phosphorylated sites and their identity are not known, the inventors synthesized several peptides corresponding respectively to the phosphorylated and acetylated forms on the serine and lysine residues of the 131-151 peptide, and studied the capacity of these peptides to be recognized by the T lymphocytes and the antibodies of lupic mice.

Figure 13:
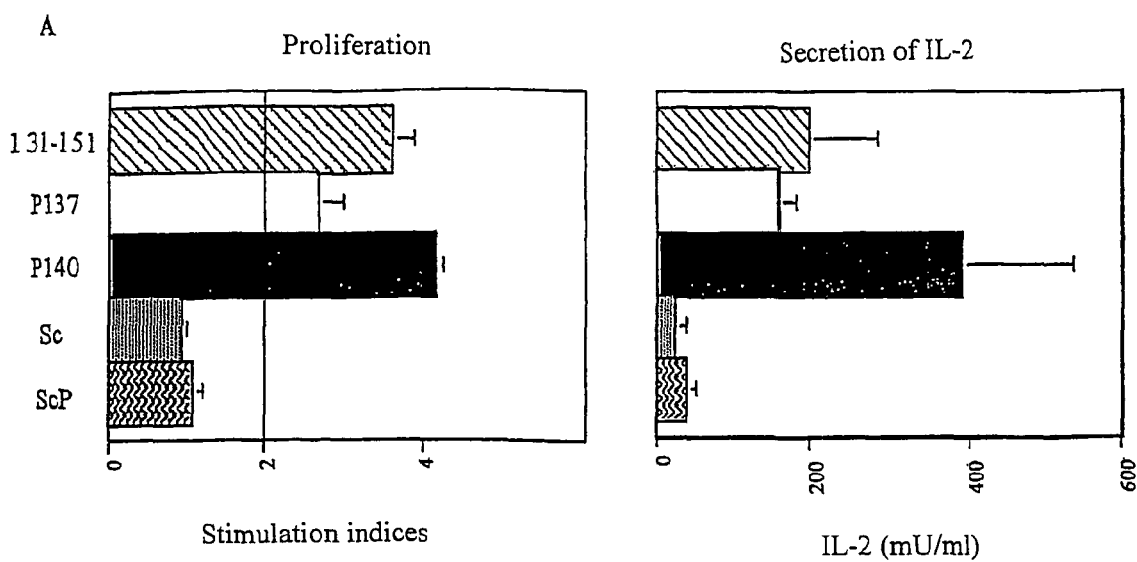

The inventors demonstrate within the scope of the present invention that the phosphorylated peptide in position 140 is recognized to the same extent as or even to a greater extent than the non-phosphorylated peptide by the CD4+ T cells and the antibodies of lupic mice (FIG. 13). The two peptides (phosphorylated in position 140 and non-phosphorylated) were used for a study of restoration of self-tolerance. These two peptides were injected by intravenous and intra-nasal route into preautoimmune mice, and the development of the disease in these mice was monitored.

The inventors have demonstrated that the administration by intravenous route but not by intranasal route of the P140 phosphorylated peptide reduces the production of large numbers of antibodies directed against the DNA, delays the appearance of glomerulonephritis and prolongs the survival of animals (FIG. 14), while the parent peptide by contrast does not induce any statistically significant effect.

Moreover, studies with 3 peptides acetylated on the lysines 138, 142 and 138+142 have been carried out. As in the case of the phosphorylated peptides, there is nothing allowing confirmation that these positions are really acetylated in vivo. The first results have shown that:

- the 3 acetylated peptides are recognized at least as well or even better than the parent peptide by the CD4+ T cells of normal mice immunized against the non-modified peptide: the proliferation rates are higher, the IL2 secretion rates are equivalent and the γ-interferon production rates are higher,
- the 3 acetylated peptides are recognized at least as well as or even better than the parent peptide by the CD4+ T cells of autoimmune mice: the proliferation rates are higher,
- the 3 acetylated peptides are recognized by the antibodies of mice directed against the parent peptide.

Finally the inventors have demonstrated that the 131-151 and P140 peptides were capable of binding various human MHC class II molecules (HLA-DR1, -DR4 and -DR11) (FIG. 19).

BIBLIOGRAPHICAL REFERENCES

Andersen M. H., Bonfill J. E., Neisig A., Arsequell G., Sondergaard I., Valencia G., Neefjes J., Zeuthen J., Elliot T. and Haurum J. S. (1999) Phosphorylated peptides can be transported by TAP molecules, presented by class I MHC molecules, and recognized by phosphorylated-specific CTL. *J. Immunol.* 163:3812-3818.

Eilat E., Zinger H., Nyska A. and Mozes E. (2000) Prevention of systemic lupus erythematosus-like disease in (NZBxNZW)F1 mice by treating with CDR1- and CDR3-based peptides of a pathogenic autoantibody. *J. Clin. Immunol.* 20:268-278.

Jouanne C., Avrameas S. and Payelle-Brogard B. (1999) A peptide derived from a polyreactive monoclonal anti-DNA natural antibody modulate lupus development in (NZBx-NZW)F1 mice. *Immunology* 96:333-339.

Kaliyaperumal A., Michaels M. A. and Datta S. K. (1999) Antigen-specific therapy of murine lupus nephritis using nucleosomal peptides: tolerance spreading impairs pathogenic function of autoimmune T and B cells. *J. Immunol.* 162:5775-5783.

Klein Gunnewiek, J. M. T. Van De Putte, L. B. A. and van Venrooij, W. J., The U1 snRNP complex: an autoantigen in connective tissue disease. *Clin. Exp. Rheumatol.* 1997, 15: 549-560.

Marino M., Ruvo M., de Fates S. and Facsina G. (2000) Prevention of systemic lupus erythematosus in MRL/lpr mice by administration of an immunoglobulin-binding peptide. Nature Biotechn. 18: 735-739.

Monneaux F., Briand J.-P. and Muller S. (2000) B and T cell immune response to snRNP in lupus mice. Autoreactive CD4+ T cells recognize a T cell epitope located within the conserved RNP consensus sequence of the 70K protein. *Eur. J. Immunol.* 20:2191-2200.

Monneaux F. and Muller S. (2000) Laboratory protocols for the identification of Th cell epitopes on self antigens in mice with systemic autoimmune diseases. *J. Immunol. Meth.* 244:195-204.

Singh R. R., Ebling F. M., Sercarz E. E. and Hahn B. H. (1995) Immune tolerance to autoantibody-derived peptides delays development of autoimmunity in murine lupus. *J. Clin. Invest.* 96:2990-2996.

Utz, P. J., and P. Anderson. (1998). Posttranslational protein modifications, apoptosis, and the bypass of tolerance to autoantigens, *Arthritis Rheum* 41: 1152-1160.

Woppmann, A. C. L. Will. U. Kornstadt, P. Zuo, J. L. Manley, and R. Lurhmann, (1993). Identification of an snRNP-associated kinase activity that phosphorylates arginine/serine rich domains typical of slicing factors. *Nucleic Acids Res* 21: 2815-2822.

Zarling A. L., Ficarro S. B., Shabanowitz J., Hunt D. F. and Engelhard V. H. (2000) Phosphorylated peptides are naturally processed and presented by major histocompatibility complex class I molecules in vivo. *J. Exp. Med.* 192:1755-1762.

KEY TO THE FIGURES

FIG. 1: recognition of the 131-151 peptide of the 70K protein by the CD4+ T cells of MRL/lpr (right column) or NZB/W lupic mice (left column); the peptide concentrations are indicated on the x-axis, the proliferation of the CD4+ T cells of MRL/lpr and BW mice, represented on the y-axis of the graphs of the first line, is measured ex vivo in the presence of the various concentrations of 131-151 peptide of the 70K protein; the proliferation is expressed in stimulation indices corresponding to the radioactivity incorporated in the DNA of the cells (in counts per minute) in the presence of peptide on the incorporation of radioactivity in the absence of peptide; the secretion of IL-2, represented on the y-axis of the graphs of the second line, is measured in the supernatants after 24 hrs of culture by a bio-assay; the IL-2 concentration is determined with a standard range of recombinant IL-2 and is expressed in mU/ml.

FIG. 2: binding of the 131-151 peptide to the molecules of the major histocompatibility complex of class II murines (I-E$^k$, I-A$^k$, I-E$^d$, I-A$^d$); fibroblasts transfected by the molecules I-E$^k$, or I-A$^k$, or I-E$^d$, or I-A$^d$ are pre-incubated with different concentrations of the 131-151 peptide; after 30 minutes at 37° C., the 12-26CI or 16-33 analogue peptides of the β2-adrenergic receptor, as well as the respective T hybridomas which recognize these peptides in the adapted context (81 for I-E$^k$, E7E9 for I-A$^k$, 26.1 for I-E$^d$, and 26.2 for I-A$^d$) are added; the supernatants are recovered after 24 hrs of culture and the secretion of IL-2 is evaluated as previously; the results are expressed as a % inhibition representing the ability of the 131-151 peptide to inhibit the binding of the 12-26 CI and 16-33β2 analogue peptides to the class II molecules.

Figure 3:
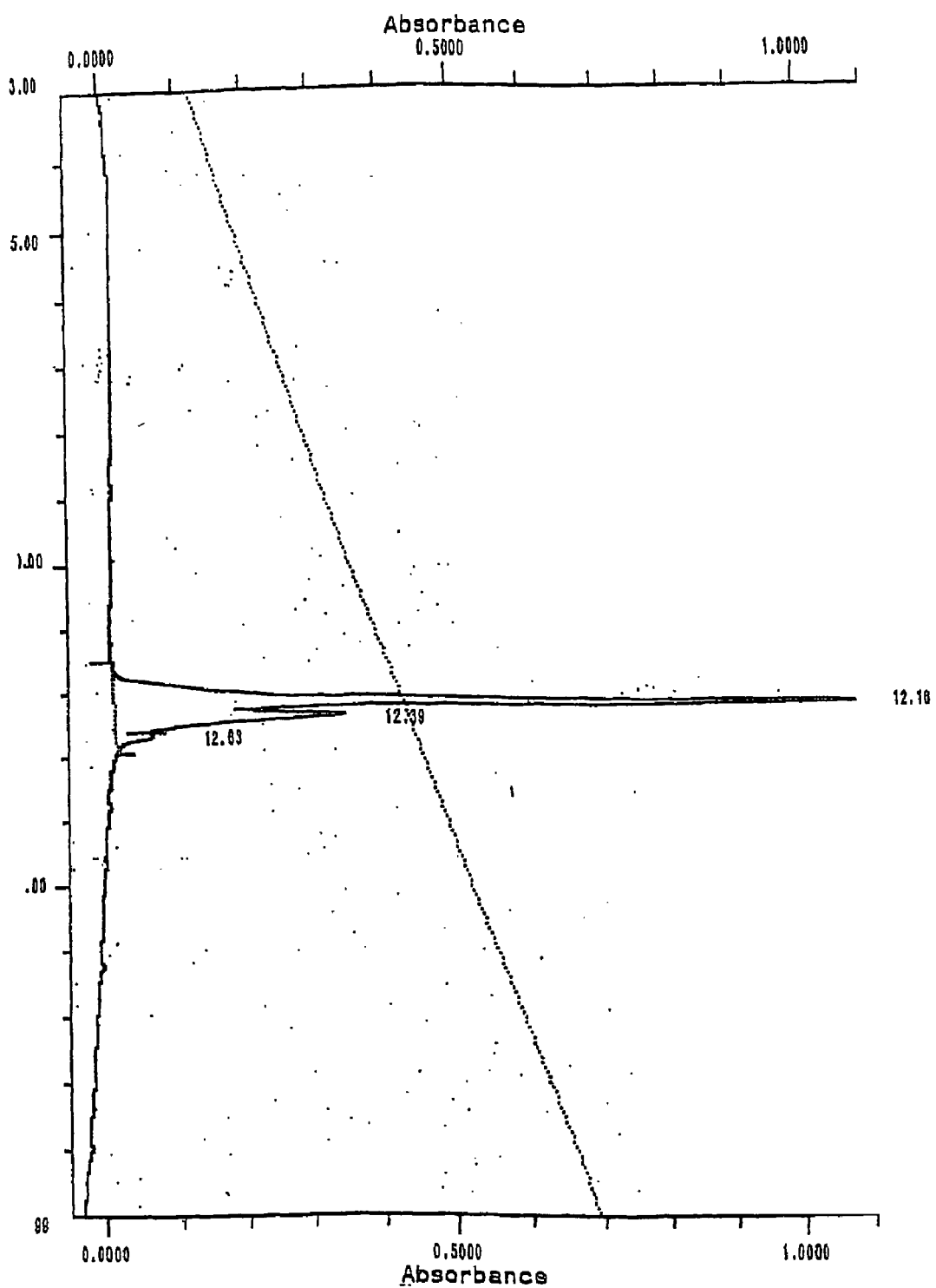
Figure 4:
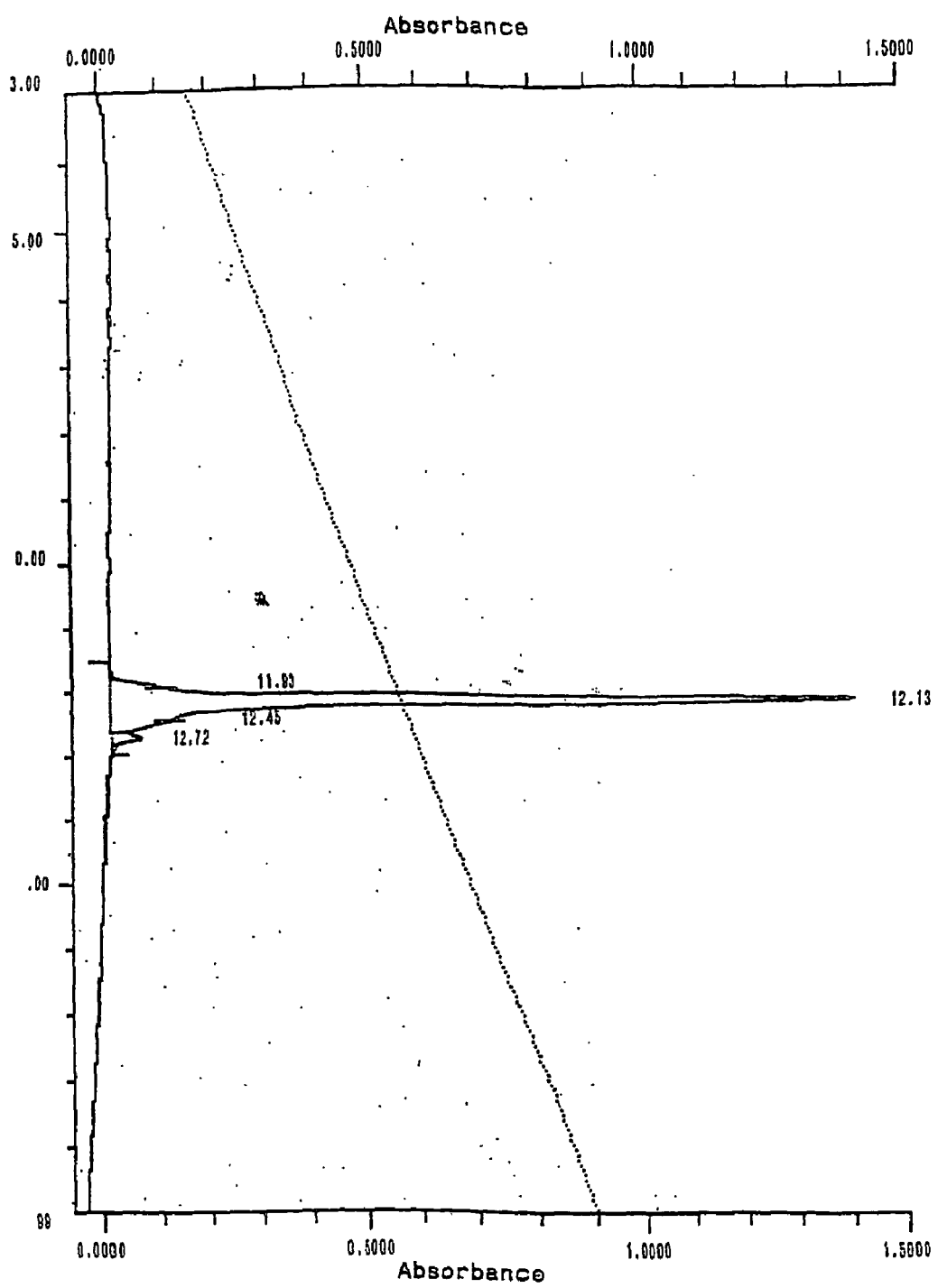
Figure 5:
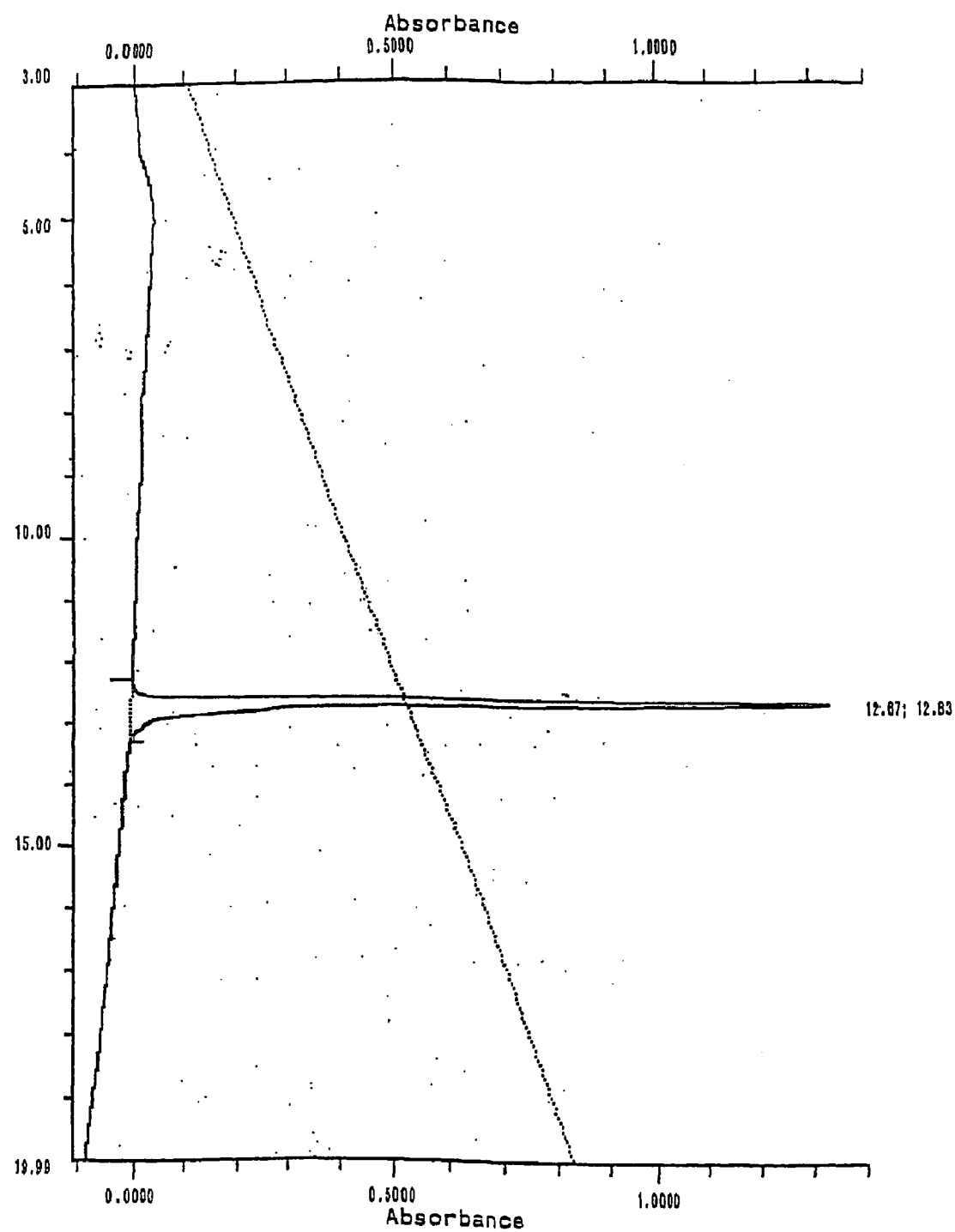
Figure 6:
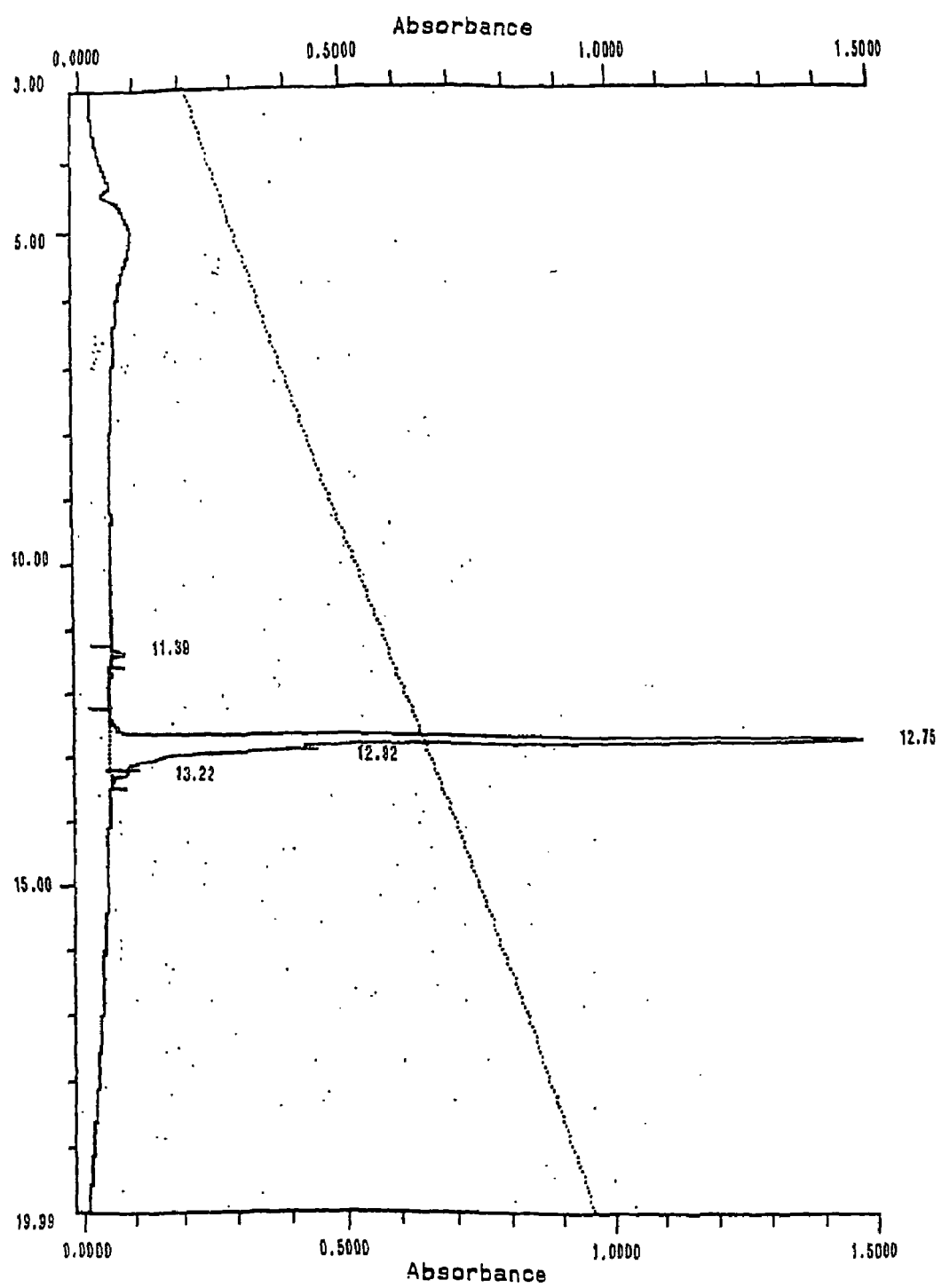
Figure 7:
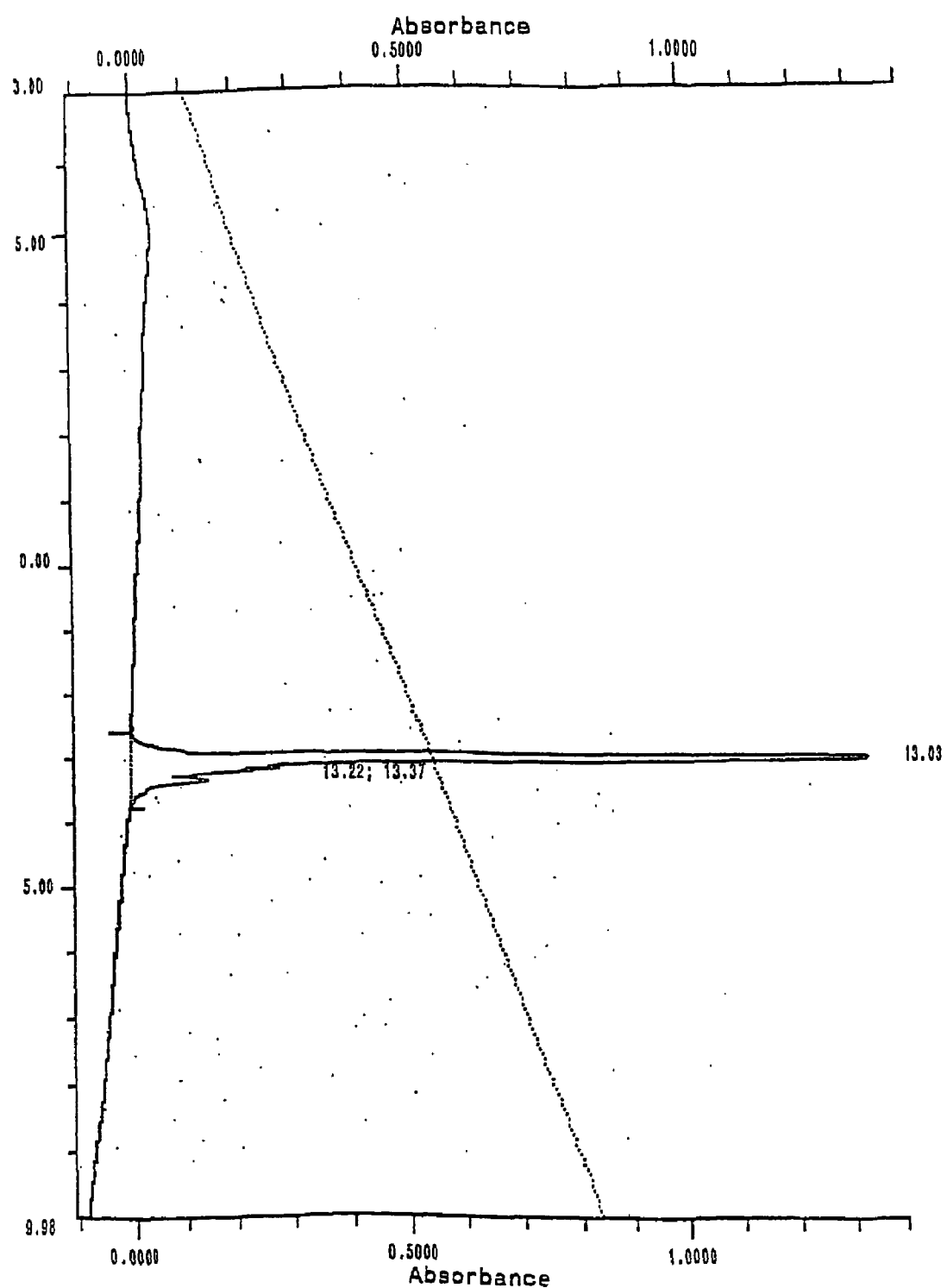
Figure 8:
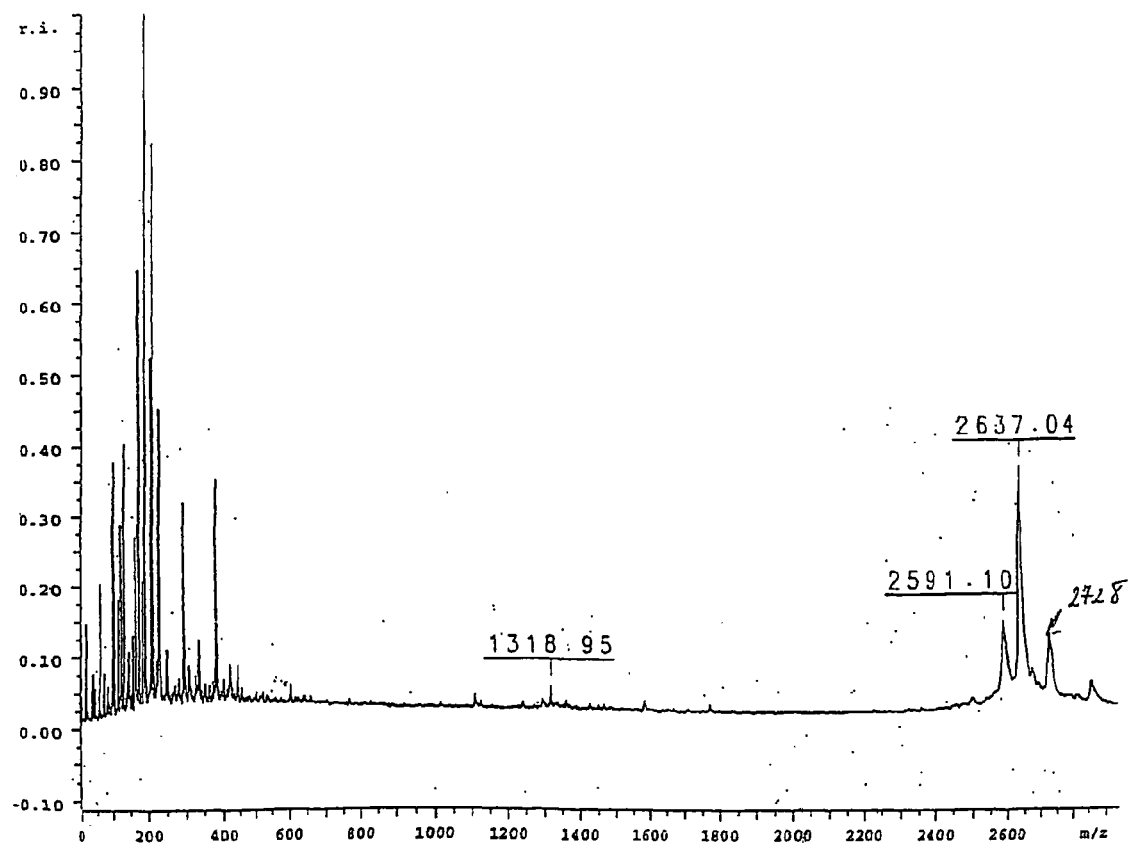
Figure 9:
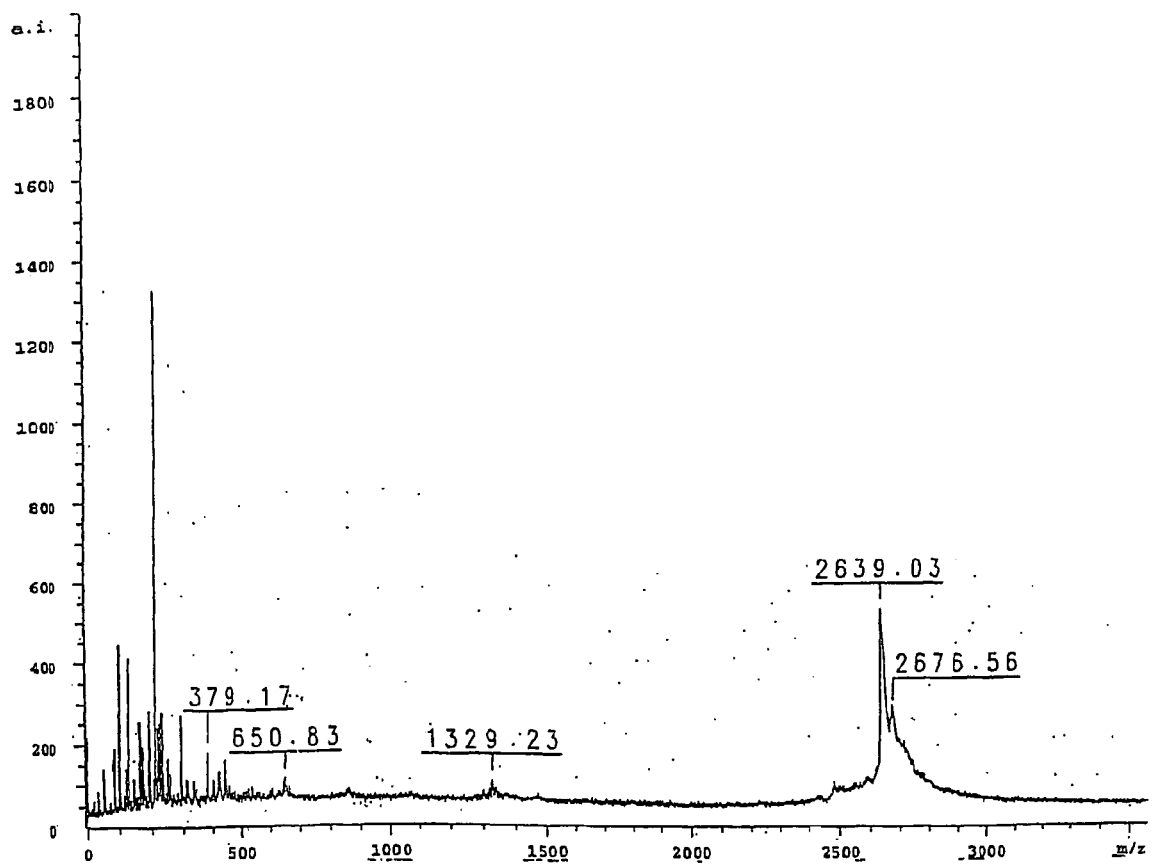
Figure 10:
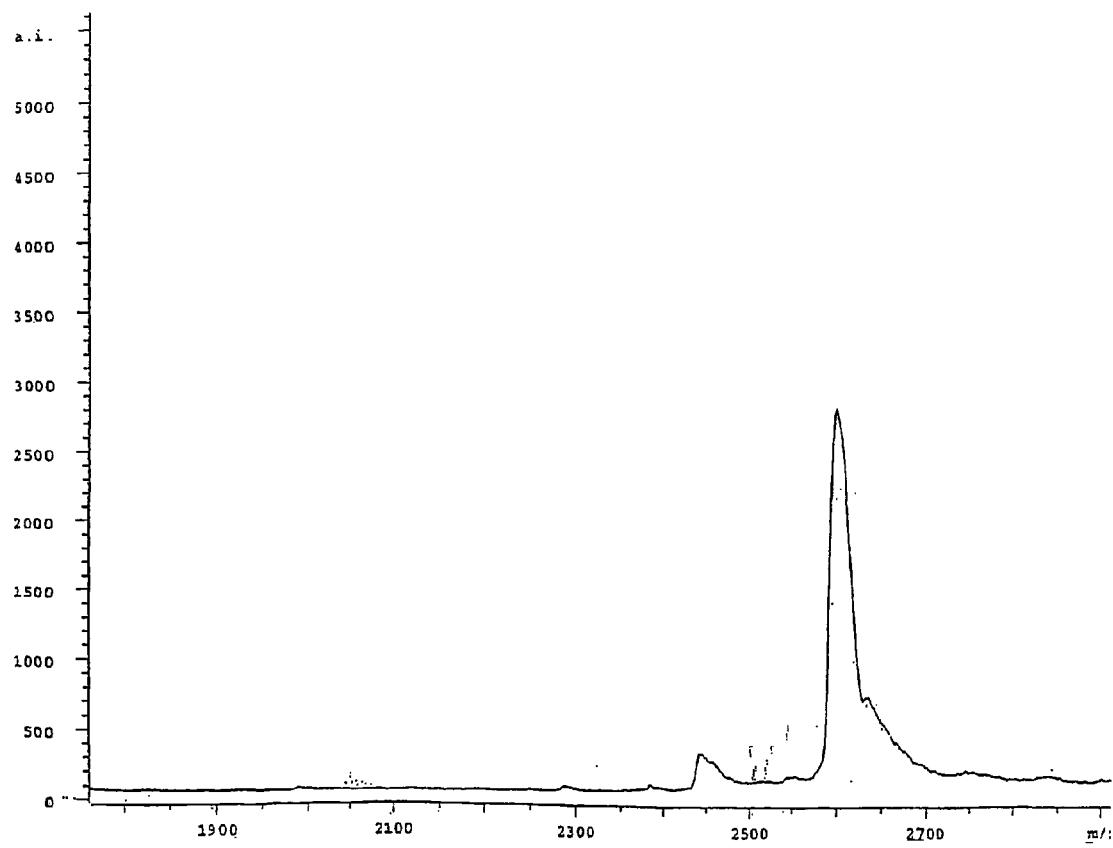
Figure 11:
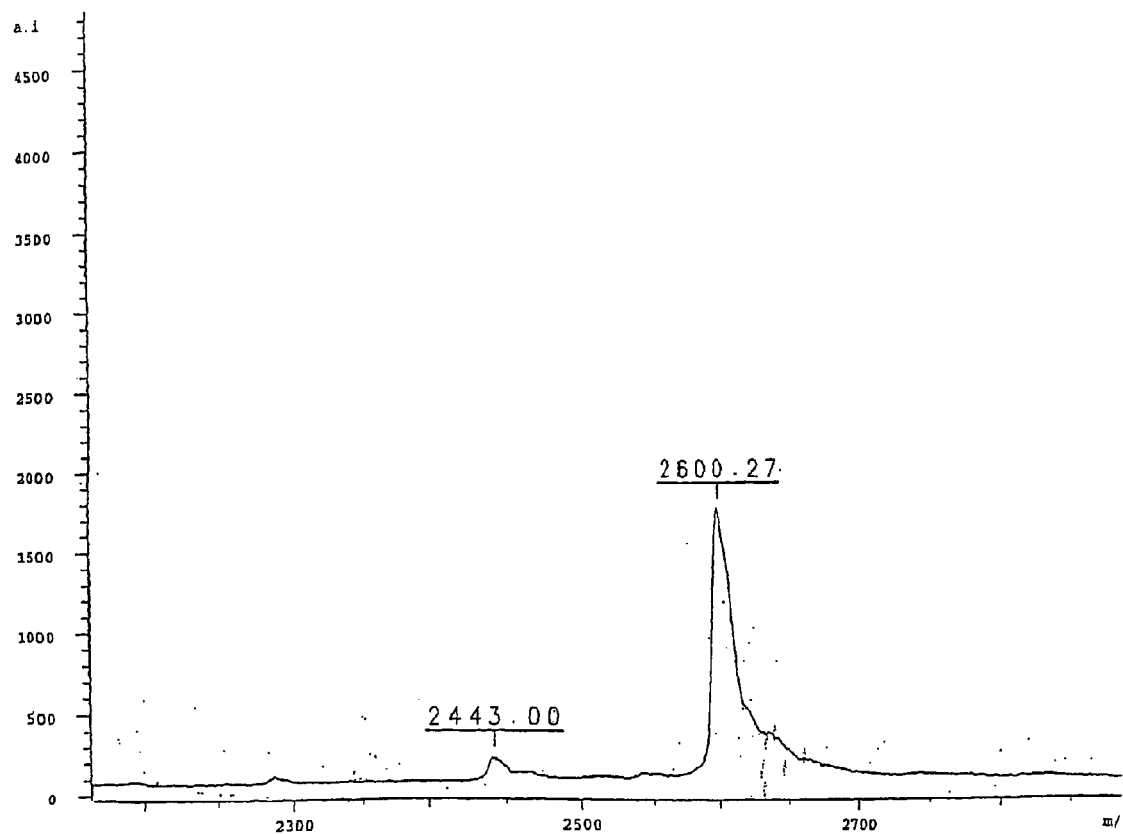
Figure 12:
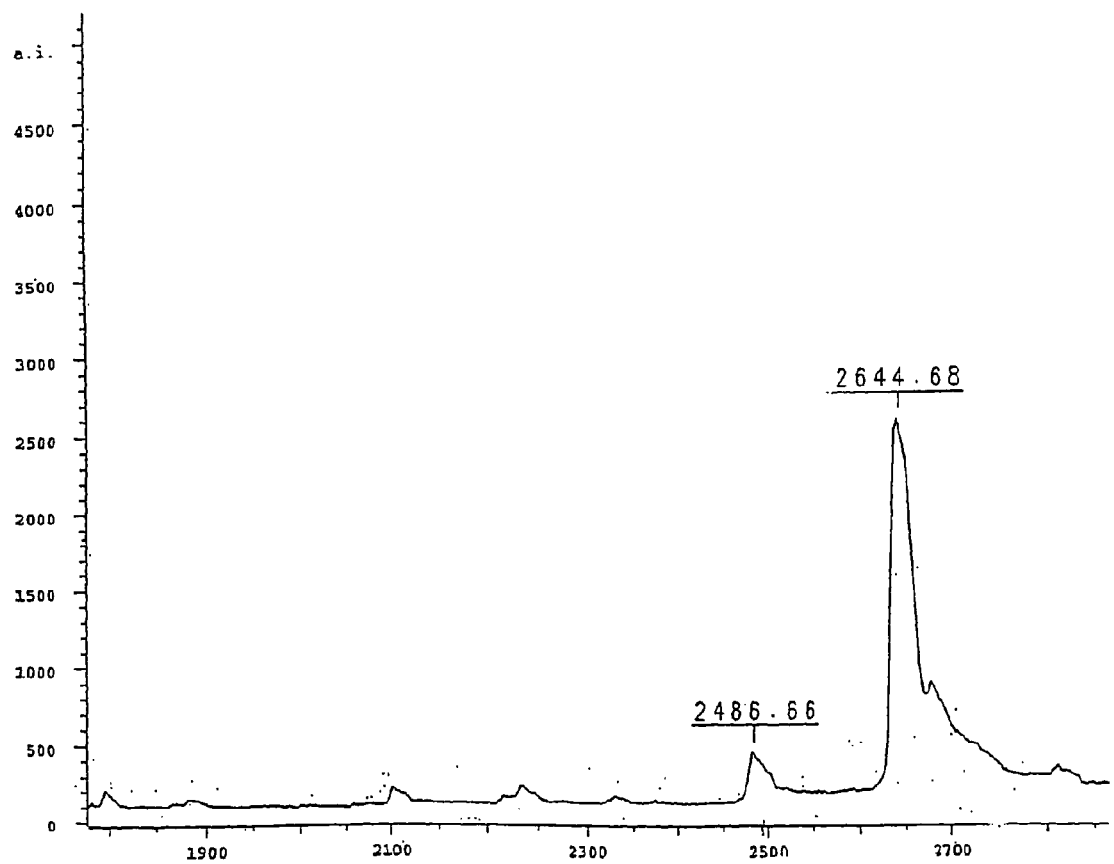

FIG. 3: HPLC profile of the P137 peptide.
FIG. 4: HPLC profile of the P140 peptide.
FIG. 5: HPLC profile of the Ac 138 peptide.
FIG. 6: HPLC profile of the Ac 142 peptide.
FIG. 7: HPLC profile of the Ac138+142 peptide.
FIG. 8: mass spectrum of the P137 peptide.
FIG. 9: mass spectrum of the P140 peptide.
FIG. 10: mass spectrum of the Ac 138 peptide.
FIG. 11: mass spectrum of the Ac 142 peptide.
FIG. 12: mass spectrum of the Ac 138+142 peptide.
FIG. 13: recognition of the P140 peptide
by the CD4$^+$ T lymphocytes (A) of MRL/lpr lupic mice; the graph on the left represents the proliferation of CD4$^+$ T cells expressed in stimulation indices as defined above in the presence of the 131-151 peptide, of the phosphorylated P137 and P140 peptides and of two scrambled peptides, phosphorylated or not phosphorylated (Sc and ScP); the positivity limit corresponds to 2.0; the graph on the right represents the secretion of IL-2 (mU/ml) in the presence of the 131-151 peptide, the P137 and P140 peptides and the Sc and ScP peptides.
and by the antibodies (B) of MRL/lpr lupic mice; the results are expressed in titre of antibodies corresponding to the dilution allowing an O.D. value at 450 nm equal to 0.2 to be obtained in an ELISA test.

Figure 14:
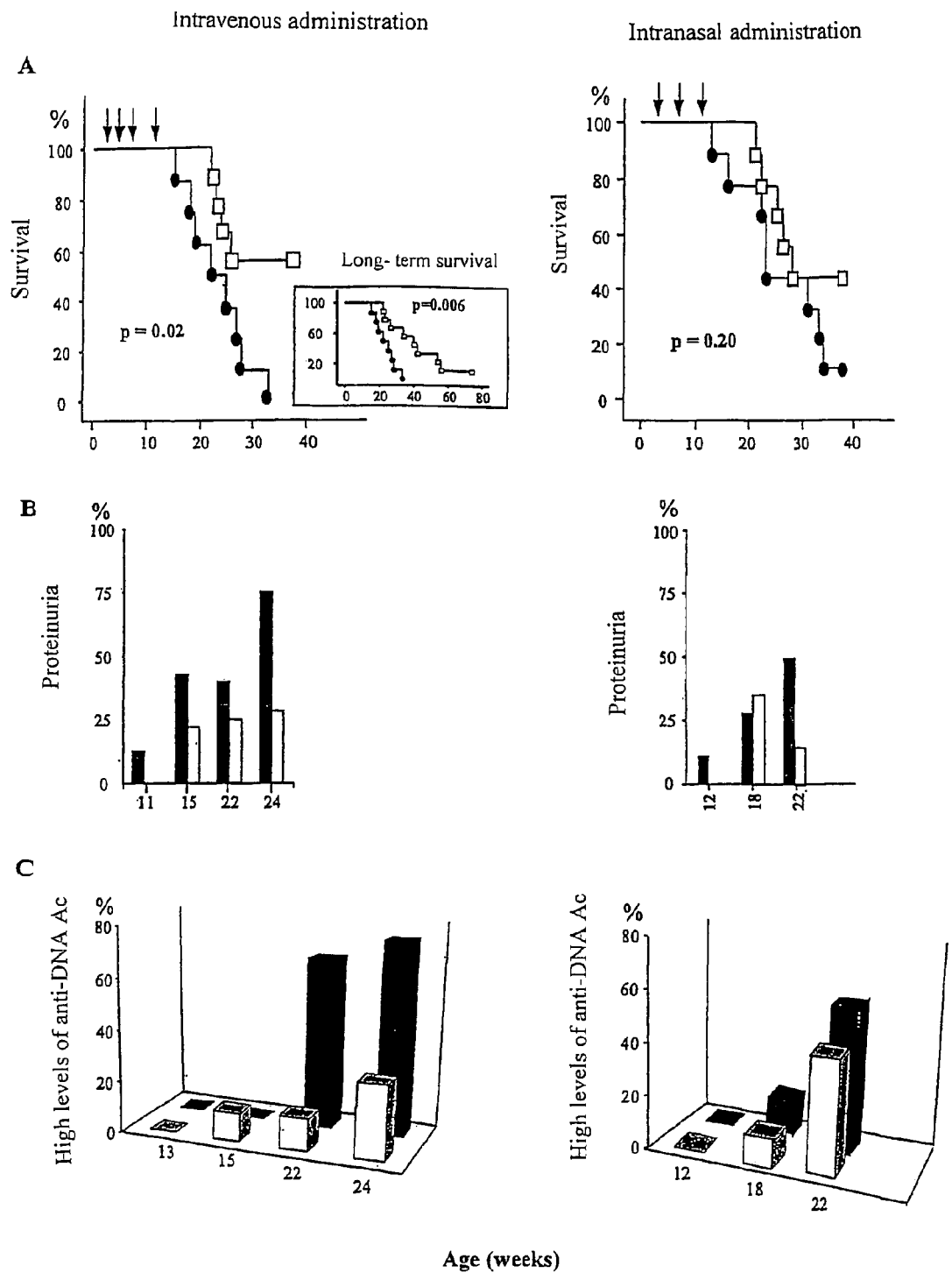

FIG. 14: effect of the administration to pre-autoimmune MRL/lpr mice of the phosphorylated form of the 131-151 peptide of the 70K protein (P140 peptide); the graph on the left represents the groups of mice which have received the peptide or the saline solution by intravenous route and the graph on the right represents the mice which have received the peptide or the saline solution by intranasal route; the results are expressed as a percentage of survival as a function of the age in weeks of the lupic mice used (A), as a percentage of positive proteinuria as a function of the age in weeks of the lupic mice used (B) and as a percentage of high rates of antibodies directed against the DNA as a function of the age of the lupic mice used (C); the administration dates are represented by arrows, the symbols and empty bars correspond to the mice having received the P140 peptide; the control group represented by the symbols and filled-in bars only received the saline solution: in the group injected with the nominal non phosphorylated 131-151 peptide, 25% of the mice survived to 35 weeks (p=0.2 compared to the control mice), and the proteinuria was hardly reduced.

Figure 15:
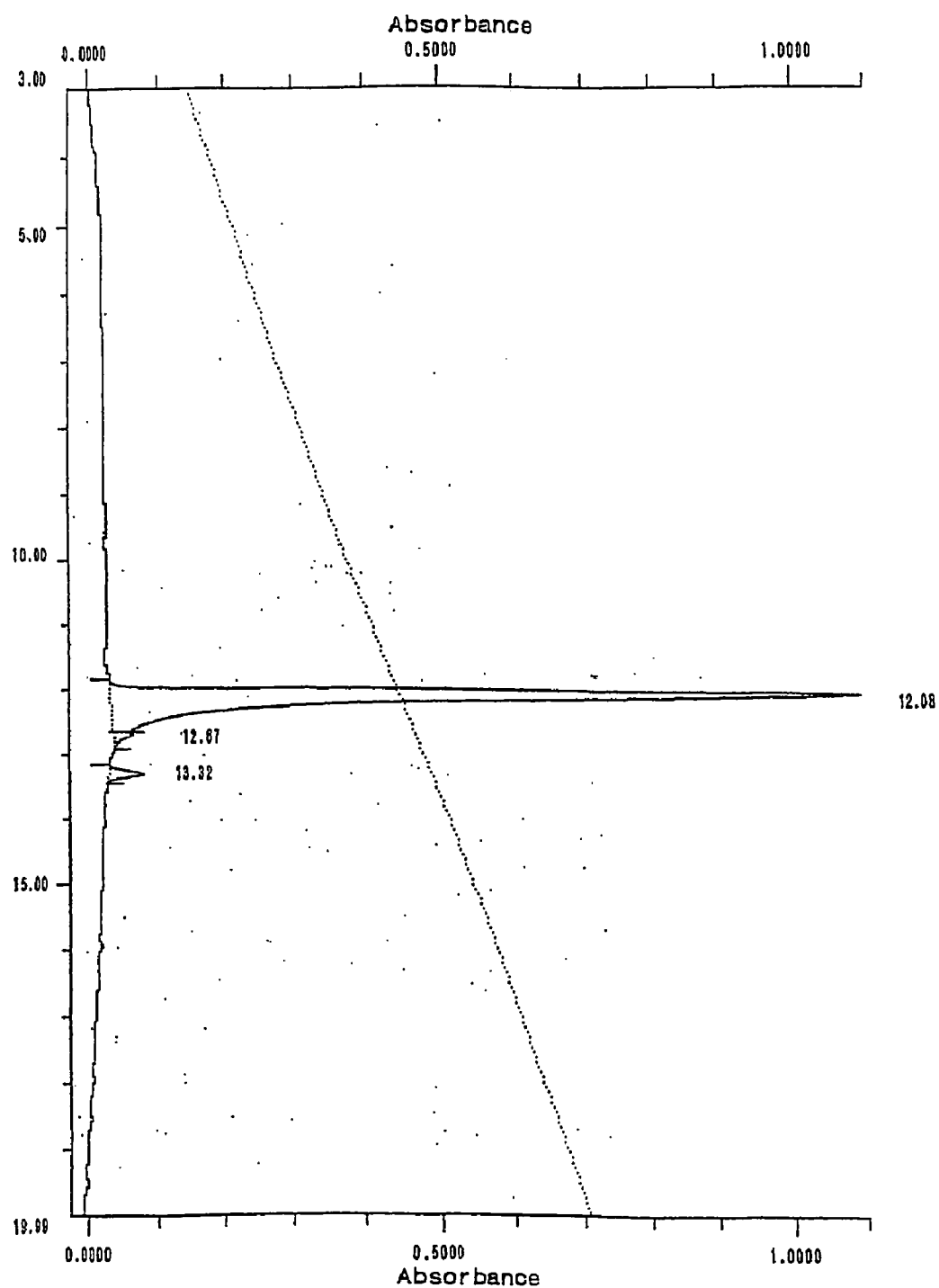
Figure 16:
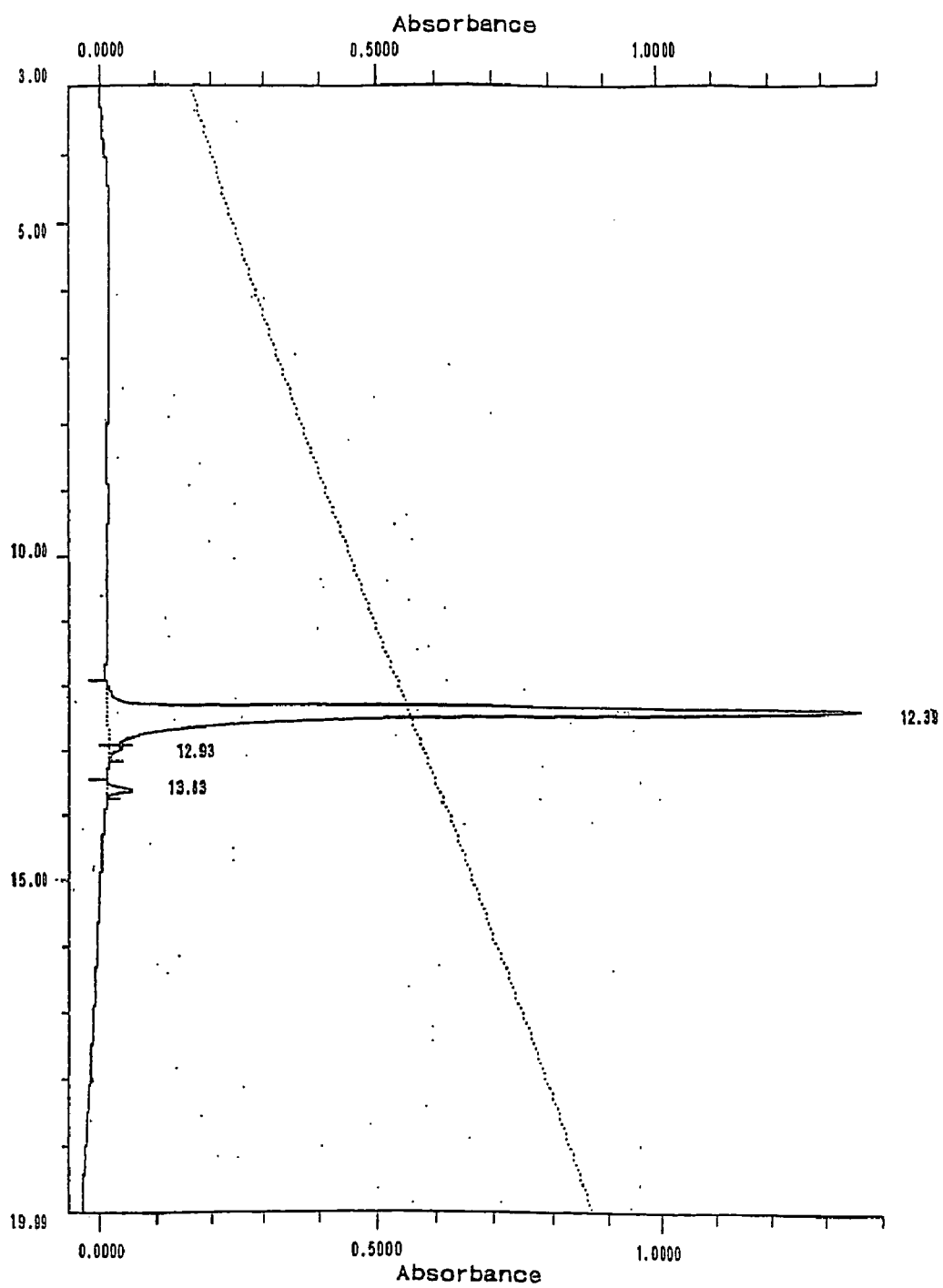
Figure 17:
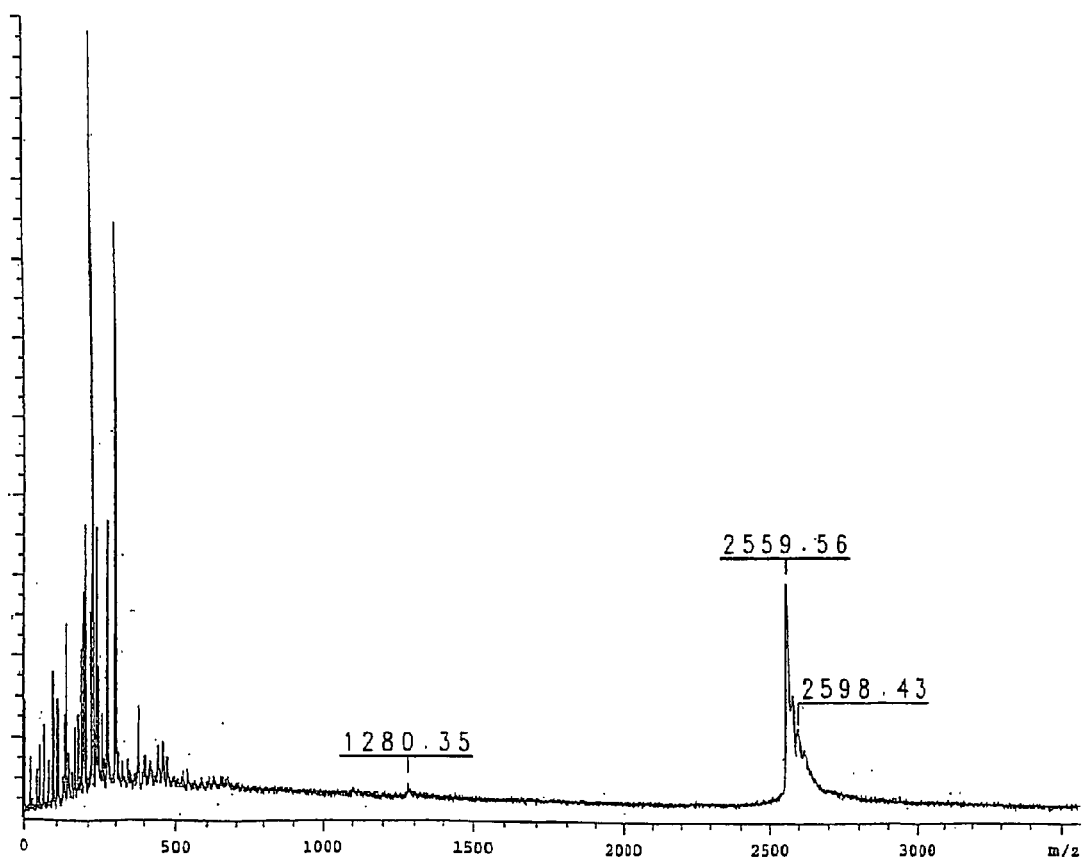
Figure 18:
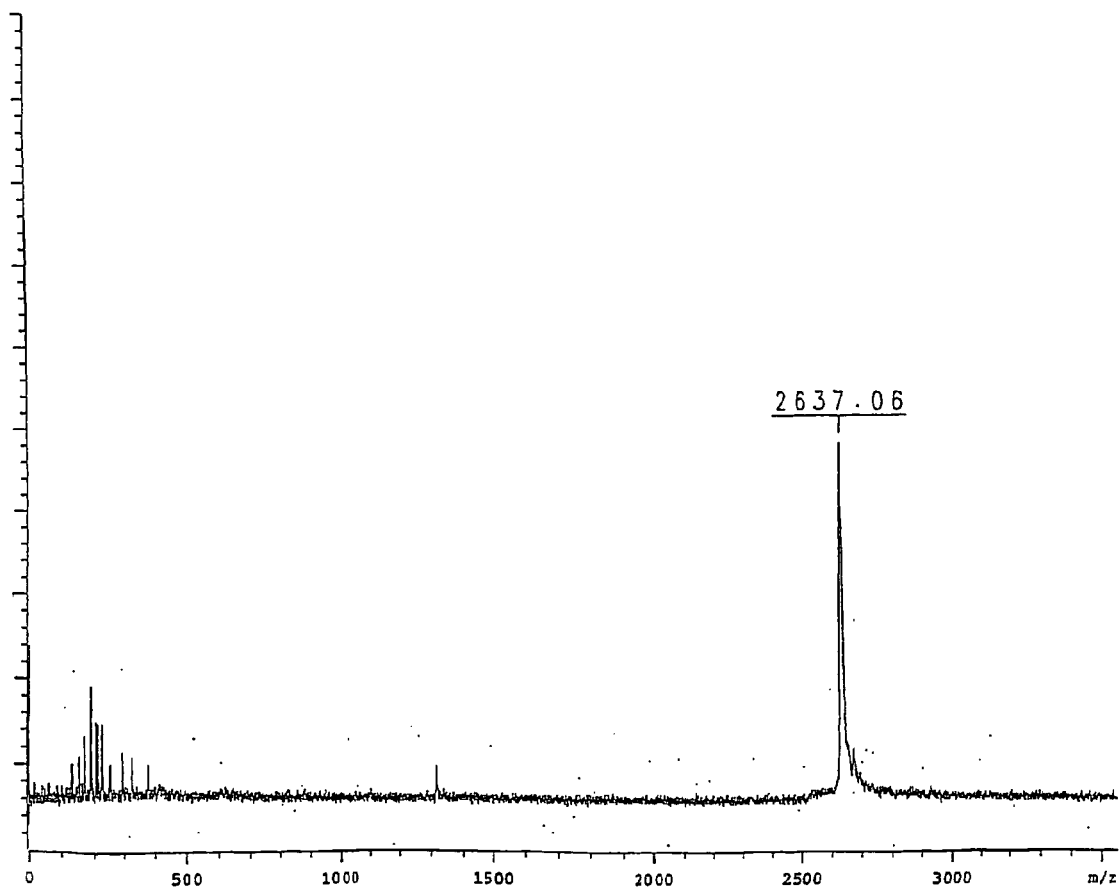

FIG. 15: HPLC profile of the Sc peptide
FIG. 16: HPLC profile of the ScP peptide
FIG. 17: mass spectrum of the Sc peptide
FIG. 18: mass spectrum of the ScP peptide
FIG. 19: binding of the 131-151 and P140 peptides to the human major histocompatibility complex class II molecules; the results are expressed as a percentage of binding of the peptides to the HLA-DR1, -DR4 and DR11 molecules; the percentage inhibition is calculated as a function of the O.D. values measured in the presence of various concentrations of 131-151 and P140 peptides (0.01-100 μM).

The invention claimed is:

1. A pharmaceutical composition comprising the isolated peptide having the amino acid sequence as set forth in SEQ ID NO: 1 wherein the serine residue in position 10 is phosphorylated, or a salt thereof, in combination with a pharmaceutically acceptable vehicle.

2. The pharmaceutical composition according to claim 1, comprising from approximately 100 ng to approximately 5 mg of said peptide.

3. The isolated peptide having the amino acid sequence as set forth in SEQ ID NO: 1 wherein the serine residue in position 10 is phosphorylated, or a salt thereof.

4. The pharmaceutical composition according to claim 1, wherein said composition comprises a salt of said peptide.

5. The isolated peptide according to claim 3, wherein said peptide is in the form of a salt.

* * * * *